United States Patent [19]

Ishizuka

[11] 4,036,234
[45] July 19, 1977

[54] DIAPER SUPPLEMENT INSERT

[76] Inventor: Haruo Ishizuka, 9-15, Ohyada 3-chome, Adachi, Tokyo, Japan

[21] Appl. No.: 764,455

[22] Filed: Jan. 31, 1977

[51] Int. Cl.$^2$ .................. A61F 13/16; A41B 13/02
[52] U.S. Cl. .................................. 128/287; 128/285; 128/290 R
[58] Field of Search ........... 128/284, 287, 288, 290 R, 128/290 W, 285

[56] References Cited

U.S. PATENT DOCUMENTS

| | | | |
|---|---|---|---|
| 2,292,030 | 8/1942 | Kraft | 128/287 |
| 2,493,492 | 1/1950 | Malamut | 128/287 |
| 3,049,124 | 8/1962 | Thompson | 128/287 |
| 3,162,196 | 12/1964 | Salk | 128/287 |
| 3,427,670 | 2/1969 | Nimoy | 128/287 X |
| 3,658,064 | 4/1972 | Pociluyko | 128/287 |
| 3,882,871 | 5/1975 | Taniguchi | 128/287 |

Primary Examiner—Aldrich F. Medbery
Attorney, Agent, or Firm—Wenderoth, Lind & Ponack

[57] ABSTRACT

The present invention provides a diaper supplement which is composed of a plurality of tricot-like fine-mesh, water-repellent, substantially oblong cloths; gauze-like coarse water-absorbent cloths of about the same size inserted between said water-repellent cloths; and a water-proof cloth of about the same size, these three kinds of cloths being adhered along the long sides at both edges.

7 Claims, 4 Drawing Figures

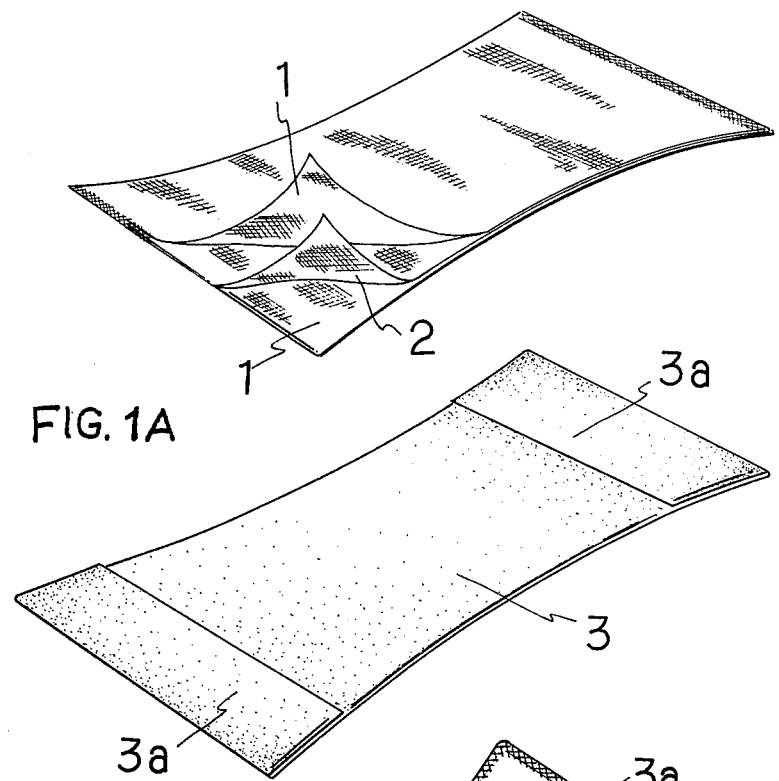
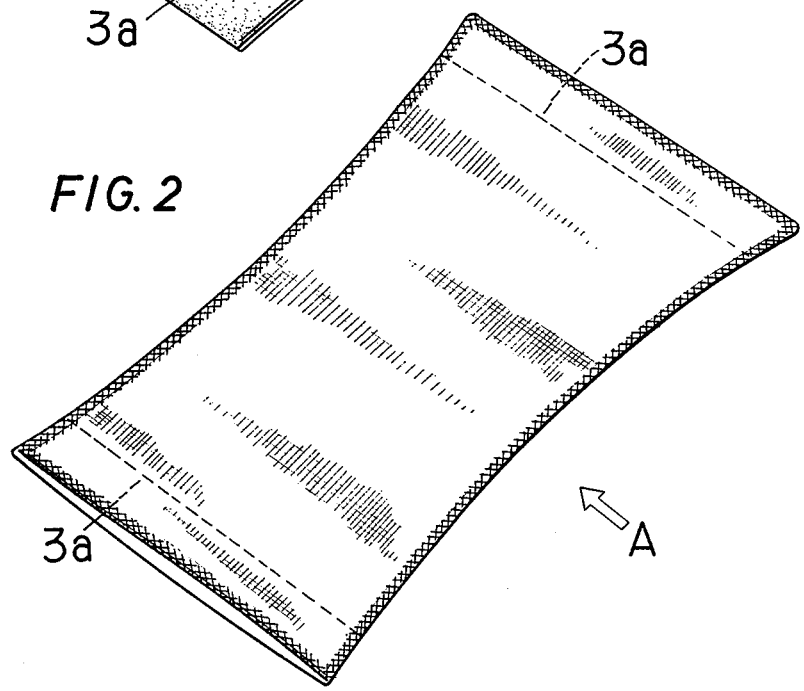

DIAPER SUPPLEMENT INSERT

BACKGROUND OF THE INVENTION

It is conventional to affix an oblong cotton cloth diaper to a baby or a paralytic patient who cannot consciously urinate. The diaper has an outer wrapper which is a waterproof cloth, which is fastened around the recipient's middle thereby preventing the recipient's environment from being soiled with unconsciously released urine. In such practice, however, the urin-soiled diaper becomes as soggy as a wet mop, giving discomfort to the baby or the patient; and prolonged contact with such wet diaper is likely to cause eczema and other skin ailments. Thus the conventional diaper is a source of discomfort to bed-ridden people and the development of a diaper free from such problems has been desired.

SUMMARY OF THE INVENTION

The present invention provides a diaper supplement which helps those who are bed-ridden, that is, a diaper supplement which can swiftly remove the urine from the skin of a baby or a paralytic patient and can swiftly dry the skin wet with urine by means of the baby's or patient's body heat itself.

To attain this purpose, the diaper supplement according to the present invention is constituted such that between a number of fine-mesh, water-repellent, tricot-like cloths of substantially oblong shape, coarse, water-absorbent gauze-like cloths of about the same size are interlarded; and a waterproof cloth of about the same size, together with said water-repellent and water-absorbent cloths, is adhered together along the long sides at both edges, e.g. by sewing or adhesive.

BRIEF DESCRIPTION OF THE DRAWINGS

The diaper supplement according to the present invention will become apparent from the following detailed description of preferred embodiments with reference to the attached drawings.

FIG. 1 is a fragmentary oblique view of the absorbent part of the diaper supplement according to the present invention.

FIG. 1A is a view of the water-proofed bottom portion of the supplement.

FIG. 2 is a whole oblique view of the diaper supplement according to the present invention.

Figure 3:
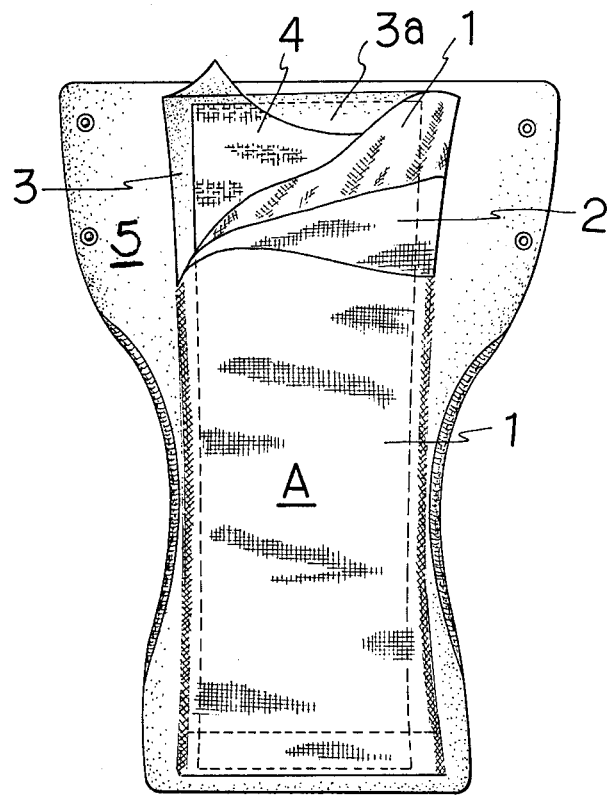
FIG. 3 is a fragmentary plan view of the diaper supplement according to the present invention in the state of being used with a conventional diaper.

DETAILED DESCRIPTION OF PREFERRED EMBODIMENTS:

Embodiments of the present invention are described with reference to the corresponding figures, in which like symbols denote like parts.

Two pieces of water-repellent tricot cloth 1, 1, a piece of water-absorbent gauze cloth 2 and a piece of water-proofed nylon cloth 3, all substantially oblong and having the shape of a section of a concave lens, are employed to make the supplement of this invention.

The short transverse sides of the waterproof nylon cloth 3 at both end or waist edges are folded over on the inside to form a bag or pocket 3a.

Between said two pieces of water-repellent cloth 1, 1 is interlarded a water-absorbent cloth 2; and the short sides of cloths 1, 1, 2 at both end edges are sewen together as seen in FIG. 1.

Said cloths 1, 1, and 2 as sewn together on the transverse short end edges and are placed on or tucked in the bag or pocket 3a of the cloth 3 and cloths 1, 1, 2 and 3 are sewn together along the long or longitudinal sides at both edges, thereby forming the diaper supplement A of the present invention.

In a practical application of this diaper supplement A, as illustrated in FIG. 3, a conventional cotton cloth diaper 4 is inserted between the integral sewed together water-repellent cloth 1 and its attached absorbent cloth 2 and the waterproof cloth 3; and the short sides of the diaper 4 at both edges are tucked into the bags 3a, 3a formed along the short sides of the waterproof cloth 3 at both edges.

The assembly of the diaper 4 and the supplement A is set, just like the conventional diaper, on the diaper cover 5 and, together with the cover 5, it is applied between a baby's legs.

When the baby urinates, the urine is absorbed by the diaper 4 after passing through the water-repellent cloth 1, the water-absorbent cloth 2 and the water-repellent cloth 1 in contact with the baby's skin. Thus the greater part of urine can be absorbed, just as in the case of a conventional diaper with no diaper supplement A of this invention, by the diaper 4. The conventional diaper, when oversaturated, can absorb no more urine and it is as if a wet cloth were applied to the skin. Besides, the urine may remain on the skin.

The diaper supplement of this invention in contrast, can dry the skin in short time. Even when the diaper 4 becomes oversaturated, the water-repellent cloth 1, which is fine-mesh, can absorb by capillary effect all the urine remaining on the skin. The urine thus absorbed is transferred to the water-absorbent cloth 2 in contact with the water-repellent cloth 1 or is diffused toward the still dry area of the water-absorbent cloth 2.

Thus use of the diaper supplement assures that no urine is left on the skin. Even after the skin is completely free of the urine, the skin will remain wet for some time, but the baby's or patient's body heat will in 1 minute or so be able to dry up the skin.

Even if the buttock part of the diaper gets oversaturated with urine, the skin can be kept near-dry, because the urine absorbed by the diaper 4 can transfer by capillary effect into the water-repellent cloth 1 coming between the diaper 4 and the skin, while the urine spread on the skin can be evaporated by the body heat; thus with the water-repellent cloth 1 acting as a spacer between the diaper 4 and the human body, the skin can be kept near-dry.

The diaper supplement of this invention being constituted as described above and applied in such manner as described above, the capillary effect of the water-repellent cloth, the quick absorption of water by the coarse water-absorbent gauze-like cloth and the user's body heat combine to dry up the water-repellent cloth close to the user's skin immediately after urination, thereby vastly contributing to the health of a baby or a bed-ridden patient by minimizing the occurrence of various skin troubles due to urination.

Moreover, an additional effect of the diaper supplement of this invention is that due to a waterproof cloth being employed, a diaper cover can be omitted for a patient lying in bed without much body movement; and in this case when the diaper supplement is directly attached to the recipient's middle by means of a strip of the waterproof cloth, the waterproof cloth will serve at the same time as the diaper cover.

Further, when the short sides at both edges of the waterproof cloth are folded back or when the water-repellent cloth and the water-absorbent cloth are sewn together along the long sides at both edges, a conventional cotton cloth diaper may easily be inserted between the waterproof cloth and the water-repellent cloth of the diaper supplement according to the present invention; and by tucking both edges of the diaper into the folded-back portion of the waterproof cloth, the diaper in use may be prevented from separating from the diaper supplement.

Furthermore, when the diaper supplement is formed like the section of a concave lens, that is, it is formed substantially oblong with the middle portion depressed, it matches the grain contour and there is no likelihood of the legs being abraded or irritated by the diaper supplement.

As understood from the above description, the diaper supplement according to the present invention has numerous practical advantages over the use of the conventional diaper alone.

What is claimed is:

1. A diaper supplement comprising:
   a. a plurality of fine-mesh water-repellent tricot-like cloths substantially oblong in shape;
   b. coarse water-absorbent gauze like cloths of the same size as (a), interlarded between said water-repellent cloths; and
   c. a waterproof cloth of about the same size as said water-repellent and water-absorbent cloths;
   said water-repellent cloths, said water-absorbent cloths and said waterproof cloth being adhered to each other along the long sides at both edges.

2. The diaper supplement of claim 1, wherein said water-repellent cloths and said water-absorbent cloths are adhered to each other along the short sides at both edges.

3. The diaper supplement of claim 1, wherein said water-repellent cloths, the surface of said water-absorbent cloths and said waterproof cloth have the shape of a section of a concave lens with the middle portion being shorter than the end portions of short side.

4. The diaper supplement of claim 1, wherein a folded-back portion is formed along the short sides at both edges of said waterproof cloth.

5. The diaper of claim 1 wherein said cloths are adhered to each other by sewing.

6. The diaper of claim 2 wherein said cloths are adhered to each other by sewing.

7. A diaper including the supplement of claim 1.

* * * * *